United States Patent [19]

Rollofson

[11] 4,303,392
[45] Dec. 1, 1981

[54] DENTAL HANDPIECE WITH QUICK DISCONNECT COUPLING

[75] Inventor: Russell L. Rollofson, Hubbard, Oreg.

[73] Assignee: A-Dec, Inc., Newberg, Oreg.

[21] Appl. No.: 55,382

[22] Filed: Jul. 9, 1979

[51] Int. Cl.³ .............................................. A61C 1/08
[52] U.S. Cl. .................................... 433/126; 285/337
[58] Field of Search .......................... 433/126, 82, 84; 285/337, 354, 33, 80, 89

[56] References Cited

U.S. PATENT DOCUMENTS

| | | | |
|---|---|---|---|
| 2,438,472 | 3/1948 | Calcott | 285/337 |
| 2,889,733 | 6/1959 | Vanderhoof | 285/337 |
| 3,175,293 | 3/1965 | Borden | 433/132 |
| 3,252,719 | 5/1966 | Borden | 433/126 |
| 3,268,205 | 8/1966 | Allen et al. | 433/132 |
| 3,789,506 | 2/1974 | Johns | 433/126 |
| 3,893,242 | 7/1975 | Lieb et al. | 433/126 |
| 3,894,338 | 7/1975 | Loge et al. | 433/82 |
| 3,921,296 | 11/1975 | Harris | 433/126 |
| 4,007,529 | 2/1977 | Fleer | 433/84 |
| 4,033,039 | 7/1977 | Lohn et al. | 433/129 |
| 4,040,311 | 8/1977 | Page, Jr. et al. | 433/129 |
| 4,104,799 | 8/1978 | Leonard | 433/129 |

FOREIGN PATENT DOCUMENTS 2004610  4/1979  United Kingdom ................ 433/126

OTHER PUBLICATIONS

"Multiflex" Brochure PR-No. 7690 /XII. 78, Kaltenback & Voigt.

Primary Examiner—Gene Mancene
Assistant Examiner—John J. Wilson
Attorney, Agent, or Firm—Klarquist, Sparkman, Campbell, Leigh, Whinston & Dellett

[57] ABSTRACT

The specification discloses a dental handpiece having a handle and a plurality of fluid tubes extending from the rearward end of the handle to the forward end of the handle. The handpiece has a coupling for connecting the rearward end of the handle to a plurality of fluid supply hoses so that each hose can deliver fluid to a corresponding one of the tubes while permitting the handle to be rotated relative to the hoses. The coupling includes a cylindrical bushing secured in the rearward end of the handle and a cylindrical connector adapted to be slidably inserted into the bushing to define an interface therebetween. The bushing and the connector having a plurality of pairs of corresponding passages. At least one passage of each pair opens in an annular groove at the interface which is contiguous with the opening of the other passage of the pair at the interface. The coupling includes a plurality of O-rings for sealing the fluid connections. A relatively large nut screwed over the rearward end of the handle can be tightened to confine a relatively large O-ring surrounding the connector to prevent the handpiece from being disconnected from the supply hoses.

6 Claims, 12 Drawing Figures

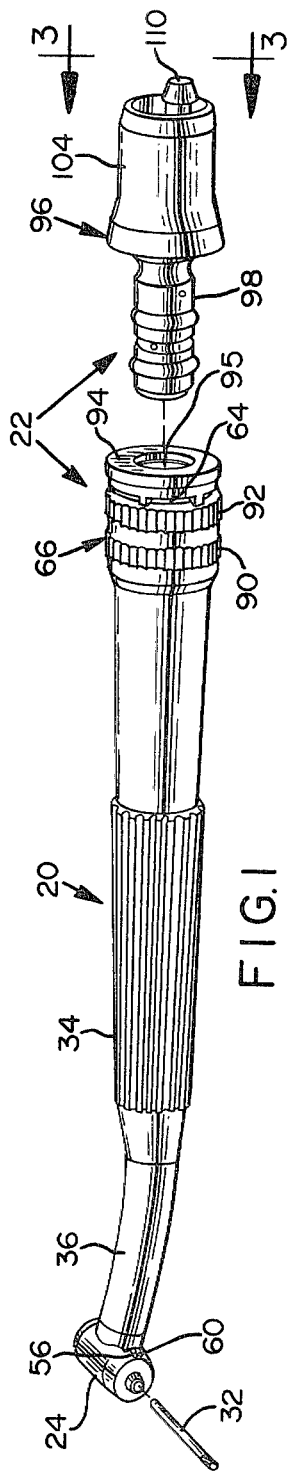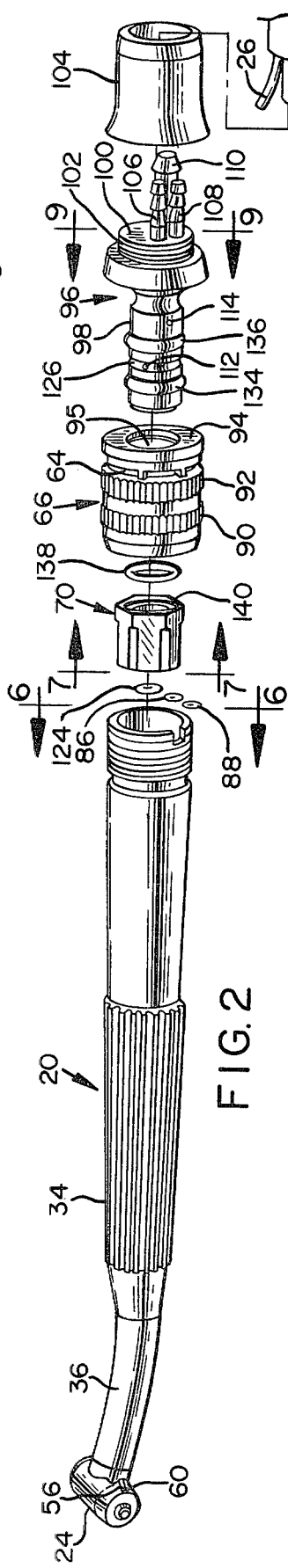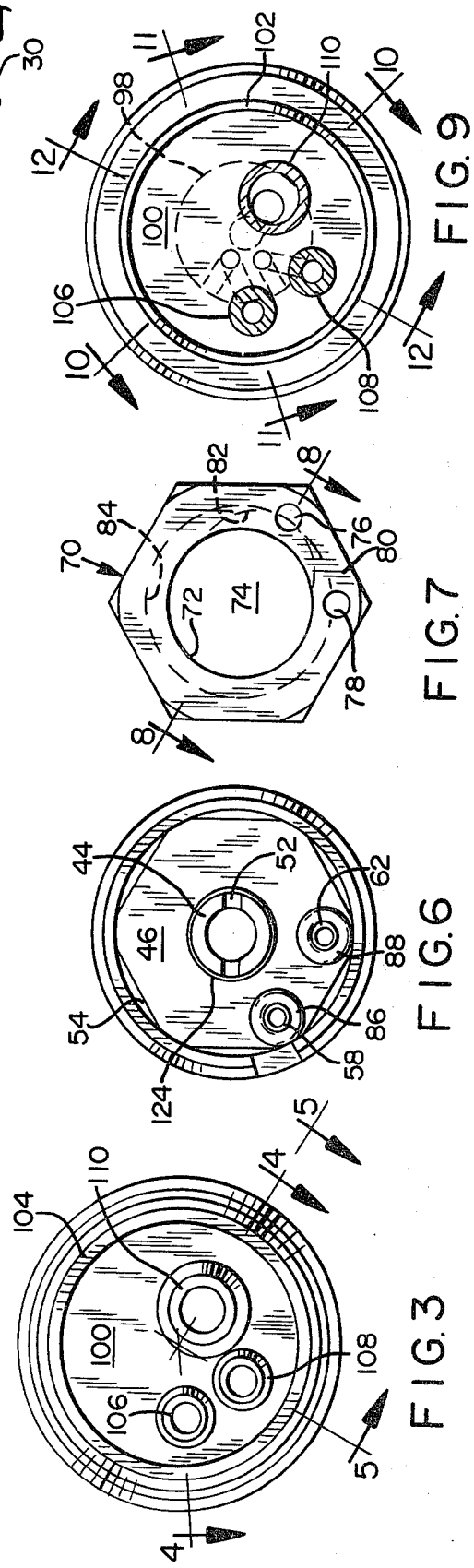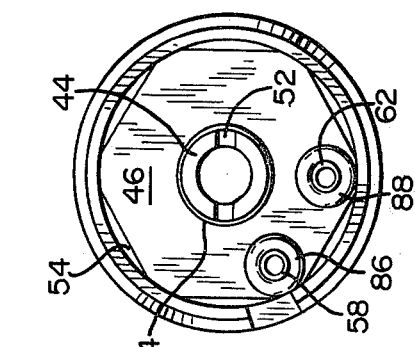

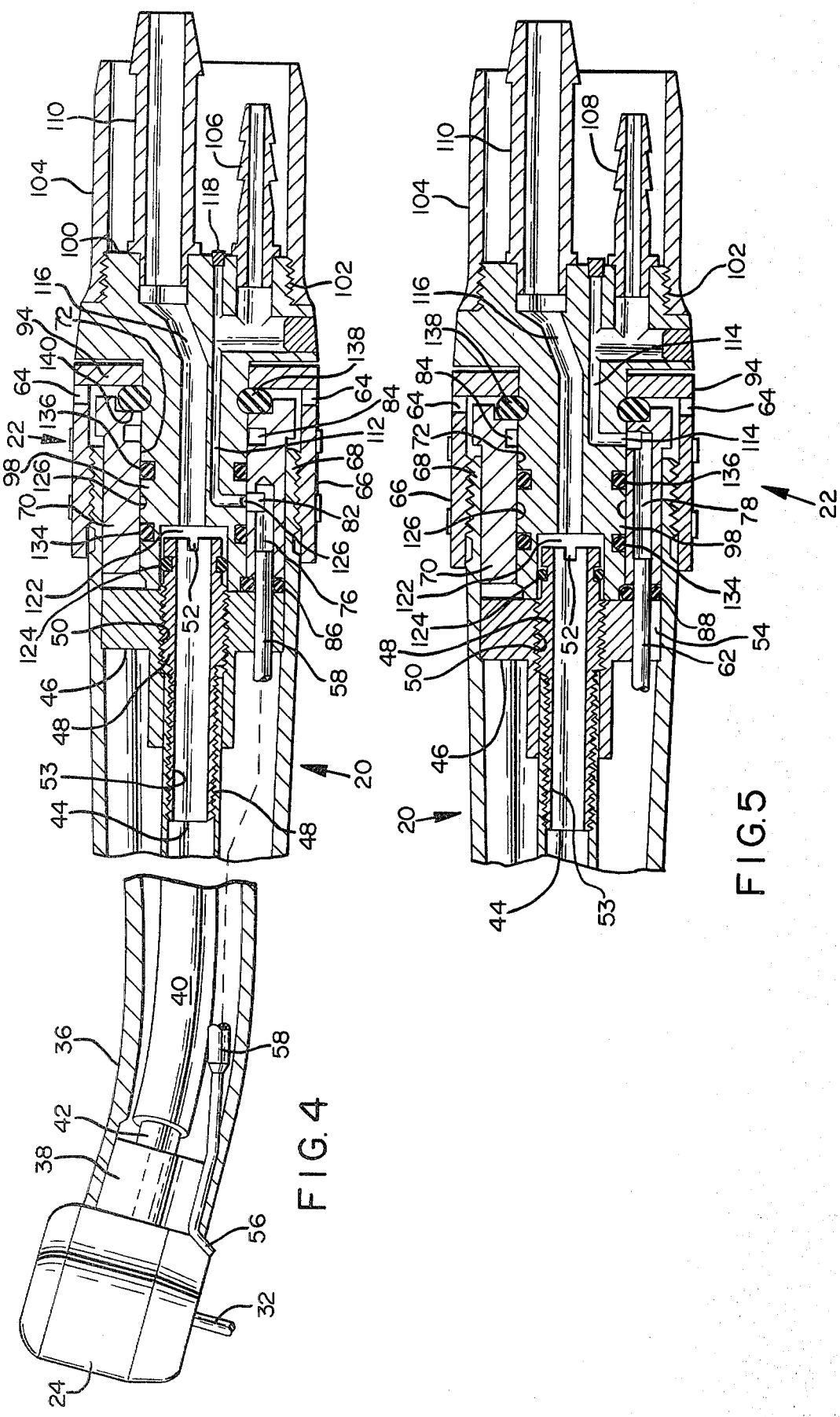

DENTAL HANDPIECE WITH QUICK DISCONNECT COUPLING

BACKGROUND OF THE INVENTION

The present invention relates to dental handpieces, and more particularly to a dental handpiece which is freely rotatable relative to its air and water supply hoses and which is adapted to be quickly disconnected from the same.

Dental handpieces are widely used by dentists for drilling and cutting teeth. They are hand-held instruments which typically include a handle, a chuck mounted in the remote end of the handle, and an air driven motor for rotating the chuck. The chuck holds an interchangeable cutting bur. High speed handpieces have air driven turbine motors which rotate their cutting burs at speeds of 250,000 RPM or more.

One such high speed dental handpiece is the Model 5000 sold by A-DEC, Inc., 2601 Crestview Drive, Newberg, Oregon, the assignee of the present application. It has a screw-on type coupling which includes individual connections for supply hoses which deliver drive air for powering its turbine motor, and coolant air and water which are directed at the tooth being drilled.

Cross contamination is one of the principal problems encountered with dental handpieces. Bacteria and viruses can be communicated from patient to patient unless the handpiece is adequately sanitized. The safest and most desirable approach is to disconnect the handpiece from the air and water supply hoses and autoclave it after each patient treatment. Furthermore, in some instances it is necessary to couple a different handpiece to the supply hoses, e.g. one which operates at a relatively lower speed and at a higher torque for tooth cleaning. Therefore, it is desirable to provide a dental handpiece with a coupling which allows the handpiece to be quickly disconnected and reconnected to the air and water supply hoses.

The use of a high speed dental handpiece requires an extraordinary degree of manipulative precision. It is desirable to provide a dental handpiece with a coupling which allows the handpiece to freely swivel or rotate relative to the air and water supply hoses. Otherwise, the dentist must compensate for the torsional forces imparted by the supply hoses when manipulating the handpiece to drill or cut a tooth. Physical fatigue and occasional resulting cutting errors can be substantially reduced by making the handpiece freely rotatable relative to the supply hoses.

However, such a coupling must provide adequate seals for the drive air, coolant air, and coolant water connections. The coolant air is generally supplied at a higher pressure than the drive air. If coolant air should leak into the conduits for the drive air the delicate turbine motor may be driven at too high of a speed. This may result in damage to the delicate bearings of the turbine motor. If coolant water should leak into the drive air conduits, the turbine motor will not operate properly.

SUMMARY OF THE INVENTION

Among the objects and advantages of the present invention are to provide:

a dental handpiece which is freely rotatable relative to its air and water supply hoses;

a dental handpiece which can be quickly disconnected and reconnected to its air and water supply hoses;

a dental handpiece which can be quickly disconnected and autoclaved;

a rotatable coupling for a dental handpiece which allows the handpiece to be freely rotated relative to its supply hoses thereby eliminating the fatiguing torsional forces normally imparted by twisting of the handpiece and the hoses during cutting and drilling;

a locking coupling for a dental handpiece which can be quickly and easily unlocked to permit the handpiece to be disconnected from its supply hoses; and a dental handpiece having a coupling for rotatably connecting the internal water and air tubes thereof to corresponding pressurized water and air supply hoses while providing water and air tight seals between the respective connections.

The present invention provides a dental handpiece having a handle and a plurality of fluid tubes extending from the rearward end of the handle to the forward end of the handle. The handpiece has a coupling for connecting the rearward end of the handle to a plurality of fluid supply hoses so that each hose can deliver fluid to a corresponding one of the tubes while permitting the handle to be rotated relative to the hoses. The coupling includes a cylindrical bushing secured in the rearward end of the handle and defining a bore which extends axially therethrough. The coupling further includes a cylindrical connector adapted to be slidably inserted into the bore of the bushing to define an interface therebetween.

The bushing and the connector have a plurality of pairs of corresponding passages, one passage of each pair extending from the forward end of the bushing to the interface and the other passage of each pair extending from the rearward end of the connector to the interface. At least one passage of each pair opens in an annular groove at the interface which is contiguous with the opening of the other passage of the pair at the interface.

Means are provided for attaching supply hoses to the rearward end of the connector so that fluid can flow from each of the hoses into one of the passages through the connector. Further means are provided for attaching tubes to the forward end of the bushing so that fluid can flow from each of the passages through the bushing into one of the tubes. Finally, locking means associated with the bushing and connector are actuable to prevent the connector from being withdrawn from the bore. The locking means are also actuable to permit the connector to be withdrawn from and inserted into the bore.

BRIEF DESCRIPTION OF THE DRAWINGS

FIG. 1 is a perspective view of a preferred embodiment of the handpiece of the present invention shown with the cylindrical connector of its coupling withdrawn from the bushing thereof;

FIG. 2 is a perspective isometric view illustrating the relationship of the components forming the coupling of the handpiece;

FIG. 3 is an elevational view of the coupling taken along lines 3—3 of FIG. 1;

FIG. 4 is a fragmentary longitudinal sectional view of the handpiece taken along lines 4—4 of FIG. 3;

FIG. 5 is a fragmentary longitudinal sectional view of the handpiece taken along lines 5—5 of FIG. 3;

FIG. 6 is an elevational view of the rearward end of the handle of the handpiece taken along lines 6—6 of FIG. 2.

FIG. 7 is an elevational view of the seal bushing forming a part of the coupling of the handpiece taken along lines 7—7 of FIG. 2;

FIG. 9 is an elevational view of the connector taken along lines 9—9 of FIG. 2;

DESCRIPTION OF THE PREFERRED EMBODIMENT

Figure 8:
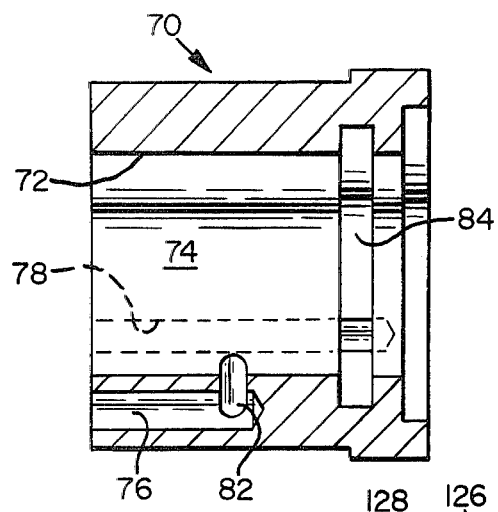
FIG. 8 is a longitudinal sectional view of the seal bushing taken along lines 8—8 of FIG. 7.

Referring to FIG. 1, the illustrated embodiment of the dental handpiece of the present invention includes a hollow stainless steel handle 20, a quick-disconnect freely rotatable coupling 22 at the rearward end of the handle, and a stainless steel impeller housing 24 at the forward end of the handle. The coupling 22 connects the handle 20 through intermediary means to be described, to individual supply hoses 26, 28 and 30 (FIG. 2) which deliver coolant air, drive air, and coolant water typically at 80 psi, 32 psi, and 40 psi, respectively. The impeller housing 24 is adapted removably to receive a cutting bur 32 or the like.

The handle 20 has an intermediate tapered portion 34 (FIG. 1) with knurling to prevent slippage when it is gripped between the dentist's fingers. It also has a somewhat upturned drive end portion 36. As best seen in FIG. 4, the impeller housing 24 has a cylindrical boss portion 38 which fits tightly into the bore of the drive end portion 36 of the handle.

The forward end of a drive air flexible plastic tube 40 (FIG. 4) fits tightly over a tube 42 carried by the boss portion 38. The rearward end of the drive air tube 40 fits tightly over an axially extending sleeve 44 carried by a locating bushing 46 fitted tightly within the rearward portion of the handle 20. The drive air tube 40 is preferably made of fluorinated ethylene propylene for high temperature resistance and for inhibiting the transmission of noise to the handle.

The sleeve 44 (FIG. 4) has an externally threaded rearward portion 48 which is screwed into an internally threaded rearward portion 50 of a bore extending axially through the locating bushing 46. The rearward end of the sleeve 44 has a screwdriver slot 52 (FIG. 6). As shown in FIG. 4, the sleeve 44 has an externally threaded forward portion 53 which is screwed into the plastic drive air tube 40, the tube being compressed between the sleeve and the locating bushing to form an airtight seal. The locating bushing 46 has a hexagonal shaped cross section (FIG. 6) and defines air passages 54 between it and the inner wall of the handle 20.

A coolant air nozzle 56 (FIG. 4) is mounted adjacent the impeller housing 24 for directing coolant air onto the cutting bur 32 and the tooth during drilling. The coolant air nozzle is connected to a one-piece metal coolant air tube 58 whose rearward end extends through a hole in the locating bushing 46. Similarly, a coolant water nozzle 60 (FIGS. 1 and 2) is mounted adjacent the coolant air nozzle 56 and is connected to a one-piece metal coolant water tube 62 (FIG. 5) whose rearward end extends through a corresponding hole in the locating bushing 46 adjacent the coolant air tube 58.

Coolant air from the hose 26 is supplied through the coupling 22 and through the tube 58 to the nozzle 56. Likewise, coolant water from the hose 30 is supplied through the coupling 22 and through the tube 62 to the nozzle 60. Drive air from the hose 28 is supplied through the coupling 22, through the bore of the sleeve 44, into the drive air tube 40 and into the impeller housing 24.

Not shown in the drawings are turbine blades which are rotatably mounted in ball bearings inside of the impeller housing 24. These blades are driven by the drive air supplied through the tube 40. The turbine blades rotate a chuck (not shown) which tightly grips the shank of the cutting bur 32. The turbine blades rotate at very high speed, e.g. about 450,000 rpm. Drive air is exhausted from the impeller housing 24 back into the bore of the handle 20 exterior of the tube 40, 58 and 62. Drive air exhausted from the impeller housing 24 flows rearwardly through the handle 20. It exits from the handle through exhaust ports 64 (FIGS. 1, 4 and 5) which extend circumferentially about a cylindrical nut 66 screwed over the externally threaded rearward portion 68 (FIGS. 4 and 5) of the handle 20.

A generally cylindrical seal bushing 70 (FIG. 2) is removably fit into the rearward end of the handle 20 rearwardly of and adjacent to the locating bushing 46 (see FIGS. 4 and 5). As shown in FIG. 7 the seal bushing 70 also has a hexagonal cross section. It further has an inner wall 72 (FIG. 8) defining a cylindrical bore 74 which extends axially and longitudinally through its center. As shown in FIGS. 4 and 5, the bore 74 of the seal bushing has a diameter considerably larger than the outside diameter of the sleeve 44 which forms an extension of the drive air tube 40.

Referring to FIGS. 7 and 8, the seal bushing 70 has coolant air and coolant water passages 76 and 78, respectively, drilled longitudinally in the wall of the seal bushing 70 from the front face 80 thereof. The passages 76 and 78 are positioned so that they can receive the coolant air and water tubes 58 and 62 (FIG. 6) therein as shown in FIGS. 4 and 5. In this manner connecting means are provided for connecting the coolant air and water tubes to the forward end of the seal bushing so that fluid can flow through each of the passages through the bushing into one of the tubes.

As best shown in FIGS. 7 and 8, the seal bushing 70 has longitudinally spaced forward and rearward recesses 82 and 84 formed in its inner wall 72. The forward recess 82 is crescent shaped and intercepts the rearward end of the coolant air passage 76 so that air can flow through the recess 82, through the coolant air passage 76 and into the coolant air tube 58. The rearward recess 84 is annular and intercepts the rearward end of the coolant water passage 78 so that water can flow through the recess 84, through coolant water passage 78 into the coolant water tube 62.

Due to the hexagonal shape of the seal bushing 70 air passages are defined between the handle 20 and the seal bushing when the bushing is tightly fit into the rearward end of the handle. Exhaust drive air can flow rearwardly through these passages to the exhaust ports 64 in the nut 66.

O-rings 86 and 88 (FIG. 6) surround the coolant air and water tubes 58 and 62. As shown in FIGS. 4 and 5, the O-rings 86 and 88 are squeezed between the locating bushing 46 and the seal bushing 70 when the coupling 22 of the handpiece is assembled. They prevent water and air from leaking into the bore of the handle 20 from the connections between the coolant air and water tubes 58 and 62 and their mating passages 76 and 78 through the seal bushing. The O-rings 86 and 88 are preferably made of an elastomeric material such as that sold under the trademark VITON. O-rings made out of this material are autoclavable.

The nut 66 has spaced apart knurled sections 90 and 92 (FIG. 1) which enable the dentist to firmly grip the nut for tightening and untightening the same. The nut 66 has a radially inwardly extending flange 94 (See FIGS. 1, 2, 4 and 5) at its rearward end which overlaps the rearward end of the seal bushing 70 and defines a hole 95 (FIGS. 1 and 2) of roughly the same diameter as the central bore 74 (FIG. 8) of the seal bushing.

The coupling 22 further includes a connector generally designated 96 in FIG. 1. The connector 96 is attached to the supply hoses 26, 28 and 30 at its rearward end and has a cylindrical neck 98 at its forward end adapted to be inserted into and withdrawn from the bore 95 of the nut 66 and the bore 74 of the seal bushing 70. The rearward end of the connector 96 which is attached to the rearward end of the neck 98 has a base 100 (FIG. 2) having an externally threaded portion 102 over which an internally threaded cylindrical supply hose connection shield 104 is screwed. The base 100 of the connector 96 carries connecting means in the form of supply barbs 106, 108 and 110 (FIGS. 2 and 3) which fit tightly within the supply hoses 26, 30 and 28, respectively.

Figure 10:
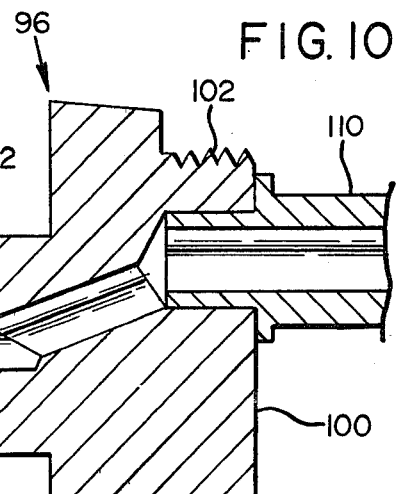
FIG. 10 is a longitudinal sectional view of the connector taken along lines 10—10 of FIG. 9.
Figure 11:
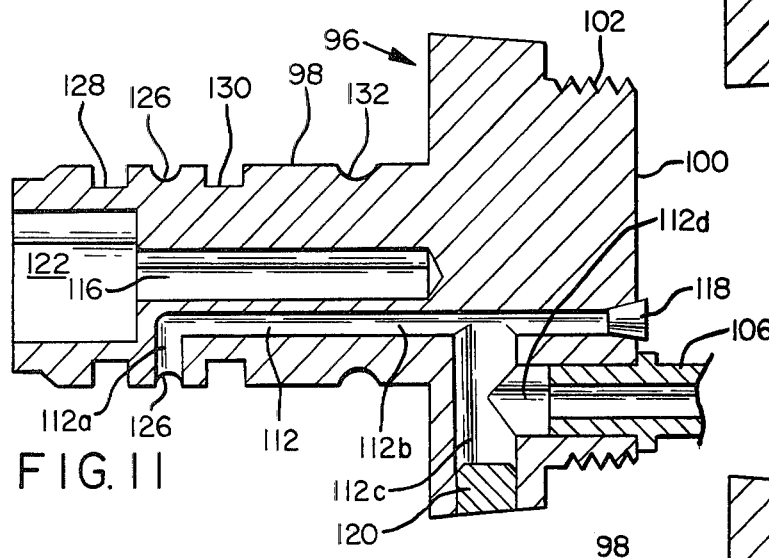
FIG. 11 is a longitudinal sectional view of the connector taken along lines 11—11 of FIG. 9.
Figure 12:
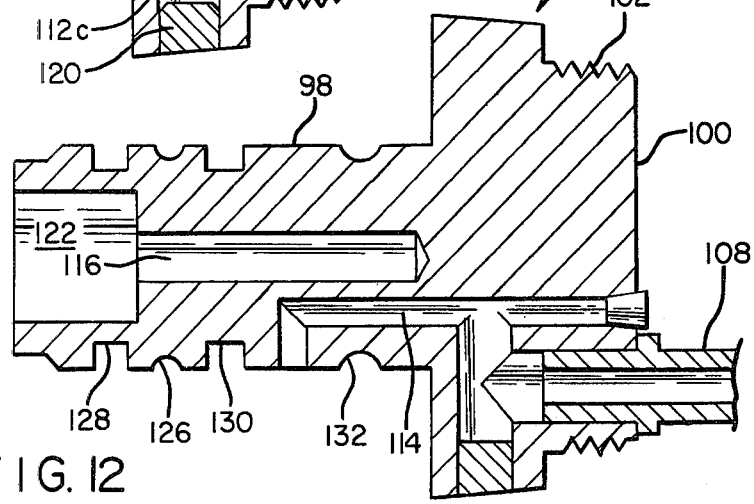
FIG. 12 is a longitudinal sectional view of the connector taken along lines 12—12 of FIG. 9.

As shown in FIGS. 10, 11 and 12, the connector 96 has three separate longitudinally extending passages 112, 114 and 116 for the coolant air, coolant water, and drive air, respectively. The passages 112, 114 and 116 are angularly disposed to one another with respect to the central axis of the connector 96. In actual practice these passages are formed by making a series of precise drills into the solid connector 96. For example, the coolant air passage 112 (FIG. 11) is formed by drilling four separate holes, 112a, 112b, 112c and 112d. The holes 112b and 112c are sealed at their rearward ends by plugs 118 and 120, respectively. The coolant air supply barb 106 is fit tightly within the hole 112d. The coolant water passage 114 is similarly formed.

The forward end of the neck 98 of the connector 96 has a cylindrical cavity 122 (FIG. 10) which communicates with the drive air passage 116. When the neck 98 is inserted in the bore 74 of the seal bushing 70 the sleeve extension 44 of the drive air tube 40 is received in the cavity 122 of the neck as shown in FIGS. 4 and 5. An elastomeric O-ring 124 (FIGS. 4 and 5) is seated in a groove surrounding the sleeve 44 and is squeezed between such sleeve and the inner wall of the cavity 122 of the neck 98 to provide a seal. This prevents drive air flowing forwardly through the passage 116 and into the bore of the sleeve 44 from leaking into the hollow bore of the handle 20. This O-ring 124 is also preferably made of a material such as that sold under the trademark VITON so that it may be autoclaved.

As shown in FIGS. 2 and 11, the forward end of the coolant air passage 112 opens into an annular groove 126 which surrounds the neck 98 and is longitudinally aligned and contiguous with the crescent shaped forward recess 82 in the seal bushing 70 (FIG. 4). The seal bushing 70 may be rotated relative to the neck 98 of the connector 96 and coolant air will still be able to continuously flow through the passage 112 in the connector 96 and into the air passage 76 extending longitudinally through the wall of the seal bushing 70. In other words, at the interface between the inner wall 72 of the seal bushing 70 and the outer surface of the neck 98 the crescent shaped recess 82 will travel about the circumference of the groove 126 which in effect provides an air passage permitting air from the passage 112 to flow therethrough into the recess 82 and into the air passage 76 in the seal bushing.

As shown in FIGS. 2, 5 and 12, the forward end of the coolant water passage 114 opens in a simple hole in the surface of the neck 98 rearward of the groove 126 and contiguous with the rearward annular recess 84 formed in the inner wall 72 of the seal bushing 70. The seal bushing 70 may be rotated relative to the neck 98, yet coolant water will still be able to be continuously supplied through the passage 114 through the connector 96 and into the passage 78 extending longitudinally through the wall of the seal bushing 70. Thus, at the interface between the inner wall 72 of the seal bushing and the outer wall of the neck 98 the annular recess 84 in effect provides a passage permitting water from the passage 114 to flow circumferentially about the neck and into the passage 78 during rotation of the seal bushing relative to the connector 96.

The neck 98 of the connector 86 has three other annular grooves 128, 130 and 132 (see FIGS. 10, 11 and 12) formed in its outer surface. Elastomeric O-rings 134 and 136 (FIGS. 2, 4 and 5) surround the neck 98 and are seated in the grooves 128 and 130, respectively. They seal the connection between the coolant air passage 112 through the connector 96 and the coolant air passage 76 through the seal bushing 70. Preferably these O-rings are also made of a material such as that sold under the trademark VITON so that they may be autoclaved.

A relatively large O-ring 138 (FIGS. 2, 4 and 5) surrounds the neck 98 and is seated in the groove 132 when the neck 98 is fully inserted in the bore 74 of the seal bushing 70. It is also seated in an annular recess 140 (FIG. 2) formed in the rearward end of the seal bushing 70. The O-ring 138 is held within the coupling 22 seated in the recess 140 by the flange 94 of the nut 66. The relatively large O-ring 138 is also preferably made of an elastomeric material such as that sold under the trademark VITON so that it can be autoclaved. When the nut 66 is screwed a predetermined amount toward the handle with the neck 98 of the connector 96 fully inserted in the bore of the seal bushing, the O-ring 138 will be confined. In this condition, the nut 66 will prevent sufficient deformation of the O-ring 128 out of the groove 132 to permit the neck 98 to be withdrawn from the bore of the seal bushing 70. Thus, when the nut is screwed down or tightened over the rearward end of the handle the handpiece cannot be disconnected from the supply hoses. Thus, the coupling provides a locking connection.

When it is desired to disconnect the handpiece from the supply hoses the nut 66 may be unscrewed so as to unconfine the relatively large O-ring 138 and permit sufficient deformation thereof out of the groove 132 in the neck so that the neck can be withdrawn or slid out of the bore of the seal bushing. When the neck is fully inserted in the seal bushing and the nut is tightened the O-rings 136 and 138 seal the connection between the coolant water passage 114 through the connector 96 and the coolant water passage 78 through the seal bushing (see FIG. 5).

Thus, when the neck of the connector is fully inserted into the bore of the seal bushing and the nut is tightened, sealed connections between the air and water supply hoses and the corresponding tubes within the handle of the handpiece are provided. At the same time the handpiece can be freely rotated relative to the supply hoses thus eliminating the torsion problem. If the dentist desires to change handpieces he or she can do so quickly merely by untightening the nut and pulling the handpiece so that the neck of the connector disengages the seal bushing. Accidental disengagement of the handpiece from the supply hoses will not occur when the nut is tightened since the confinement of the O-ring 138 by the nut provides a positive locking mechanism. Once disconnected the handpiece may be placed into an autoclave for sterilization. If O-rings made of the aforementioned preferred material have been utilized they need not be removed prior to the autoclaving process.

Having described a preferred embodiment of the present invention it will be apparent that the invention permits of modification in arrangement and detail. I claim all such modifications as come within the true spirit and scope of the following claims.

I claim:

1. A dental handpiece comprising:
   a handle,
   a plurality of tubes extending within the handle from its rearward end to its forward end,
   coupling means at the rearward end of the handle for connecting the handle to a plurality of fluid supply hoses so that each hose can deliver fluid to a corresponding one of the tubes while permitting the handle to be rotated relative to the hoses,
   the coupling means including a seal bushing at the rearward end of the handle, the seal bushing having an inner wall defining a cylindrical bore and a plurality of passages extending rearwardly from the forward end of the seal bushing and opening in axially spaced recesses in the inner wall, the passages receiving corresponding ones of the tubes in their forward ends,
   a connector having a cylindrical neck at its forward end slidably inserted in the bore and means at its rearward end for attaching the fluid supply hoses,
   the connector having a plurality of passages each corresponding to a passage through the seal bushing, the connector passages extending from the hose attaching means to axially spaced recesses in an outer wall of the neck, each connector recess being contiguous with a seal bushing recess to define mating pairs, at least one recess of each pair being annular so that fluid can flow continuously through the corresponding passages when the seal bushing is rotated relative to the connector,
   said handle including an externally threaded cylindrical portion at its rearward end,
   said coupling means including an internally threaded cylindrical nut screwed over the externally threaded handle portion and having a radially inwardly extending flange overlapping the rearward end of the seal bushing,
   said neck having an annular locking groove positioned adjacent the rearward end of the seal bushing,
   and an elastomeric locking O-ring positioned between the rearward end of the seal bushing and the flange and seated in the locking groove, the nut capable of being screwed a predetermined amount toward the handle to confine the O-ring and prevent sufficient deformation thereof out of the groove to permit the neck to be withdrawn from the bore.

2. The dental handpiece of claim 1 wherein the neck has a cavity in its forward end and the connector has a passage which extends from the hose attaching means centrally through the neck to the cavity, the cavity slidably receiving one of the tubes.

3. The dental handpiece of claim 2 including a locating bushing in the rearward end of the handle forward of the seal bushing, the locating bushing having a central passage through which the one tube extends and adjacent passages through which the other tubes extend.

4. The dental handpiece of claim 3 including sealing O-rings which are squeezed between the locating bushing and the seal bushing and surround the tubes which are received in the passages through the seal bushing.

5. The dental handpiece of claim 1 including a plurality of sealing O-rings squeezed between the neck and the seal bushing to seal the connections between the corresponding passages through the neck and the seal bushing.

6. A dental handpiece comprising:
   a hollow handle having an externally threaded cylindrical portion at its rearward end and adapted to receive an air driven impeller means at its forward end;
   an air nozzle at the forward end of the handle;
   a water nozzle at the forward end of the handle;
   a drive air tube extending longitudinally through the handle for delivering air to the impeller means;
   a coolant air tube extending longitudinally through the handle for delivering air to the air nozzle;
   a coolant water tube extending longitudinally through the handle for delivering water to the water nozzle;
   a locating bushing fit into the rearward end of the handle and having a central hole through which the drive air tube extends, and adjacent holes through which the coolant air tube and the coolant water tube extend, the locating bushing and the handle defining an air passage therebetween through which exhaust drive air can flow;
   a seal bushing fit into the rearward end of the handle rearwardly of and adjacent to the locating bushing, the seal bushing having an inner wall defining a cylindrical bore which extends longitudinally through its center, the bore having a larger diameter than the outside diameter of the drive air tube, the seal bushing having longitudinally extending coolant air and coolant water passages, for receiving the coolant air tube and the coolant water tube, respectively, the coolant air passage being shorter than the coolant water air passage, the seal bushing further having longitudinally spaced forward and rearward recesses in its inner wall, the forward recess intercepting the air passage in the seal bushing and the rearward recess being annular and intercepting the water passage in the seal bushing, the seal bushing and the handle defining an air passage therebetween through which exhaust drive air can flow;
   an internally threaded cylindrical nut screwed over the externally threaded rearward portion of the handle and having a radially inwardly extending flange at its rearward end overlapping the rearward end of the seal bushing, the nut having exhaust ports through which exhaust drive air can escape;

a connector rearward of the locating bushing and having a cylindrical neck at its forward end slideably inserted in the bore through the seal bushing, the neck having a cavity in its forward end in which the drive air tube is slideably inserted, the connector further having a rearward end including barbs for attaching drive air, coolant air, and coolant water supply hoses thereto, the connector further having a first passage which extends from the drive air barb centrally through the neck to the drive air tube, a second passage which extends from the coolant barb through the neck and opens into a first annular groove surrounding the neck and contiguous with the foward recess of the seal bushing, and a third passage which extends from the coolant water barb through the neck and opens in a contiguous relationship with the rearward annular recess of the seal bushing, the neck further having a second annular groove positioned adjacent the rearward end of the seal bushing;

a first elastomeric O-ring surrounding the coolant air tube and squeezed between the locating bushing and the seal bushing;

a second elastomeric O-ring surrounding the coolant water tube and squeezed between the locating bushing and the seal bushing;

a third elastomeric O-ring surrounding the drive air tube and squeezed between the drive air tube and the neck;

a fourth elastomeric O-ring surrounding the neck forward of the first annular groove and squeezed between the neck and the seal bushing;

a fifth elastomeric O-ring surrounding the neck rearward of the first annular groove and forward of the opening of the third passage in the neck, the fifth O-ring squeezed between the neck and the seal bushing; and a sixth elastomeric O-ring positioned between the rearward end of the seal bushing and the flange and seated in the second annular groove surrounding the neck, the nut capable of being screwed a predetermined amount toward the handle to confine the sixth O-ring and prevent sufficient deformation thereof out of the second groove to permit the neck to be withdrawn from the bore.

* * * * *

UNITED STATES PATENT AND TRADEMARK OFFICE
CERTIFICATE OF CORRECTION

PATENT NO. : 4,303,392
DATED : December 1, 1981
INVENTOR(S) : Russell L. Rollofson It is certified that error appears in the above—identified patent and that said Letters Patent is hereby corrected as shown below:

Column 9, line 18, after "coolant" insert --air--;

line 20, change "foward" to --forward--.

Signed and Sealed this

Sixteenth Day of February 1982

[SEAL]

Attest:

GERALD J. MOSSINGHOFF

Attesting Officer

Commissioner of Patents and Trademarks